(12) United States Patent
Agus (10) Patent No.: US 7,425,565 B2
(45) Date of Patent: Sep. 16, 2008

(54) USE OF BENZOTHIOPENES TO TREAT AND PREVENT PROSTATE CANCER

(75) Inventor: David B. Agus, Beverly Hills, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 693 days.

(21) Appl. No.: 10/625,152

(22) Filed: Jul. 23, 2003

(65) Prior Publication Data
US 2004/0132776 A1 Jul. 8, 2004

Related U.S. Application Data

(63) Continuation-in-part of application No. 10/142,087, filed on May 9, 2002, now abandoned.

(51) Int. Cl.
*A61K 31/445* (2006.01)
(52) U.S. Cl. .................................................. 514/320
(58) Field of Classification Search ................... None
See application file for complete search history.

(56) References Cited

U.S. PATENT DOCUMENTS

| | | | |
|---|---|---|---|
| 4,133,814 | A | 1/1979 | Jones et al. |
| 4,358,593 | A | 11/1982 | Jones et al. |
| 4,418,068 | A | 11/1983 | Jones |
| 5,135,849 | A | 8/1992 | Soto et al. |
| 5,795,909 | A | 8/1998 | Shashoua et al. |
| 5,821,254 | A | 10/1998 | Sporn et al. |
| 5,889,042 | A | 3/1999 | MacLean et al. |
| 5,945,412 | A | 8/1999 | Fuh et al. |
| 5,962,505 | A | 10/1999 | Bobrove et al. |
| 6,099,823 | A | 8/2000 | Falb |
| 6,121,292 | A | 9/2000 | Chandrasekhar et al. |
| 6,124,311 | A | 9/2000 | Chandrasekhar et al. |
| 6,159,696 | A | 12/2000 | Dijkema et al. |
| 6,204,286 | B1 | 3/2001 | Cameron et al. |
| 6,225,308 | B1 | 5/2001 | Miller et al. |
| 6,632,447 | B1 * | 10/2003 | Steiner et al. ............... 424/434 |
| 2003/0158164 | A1 | 8/2003 | Ohta et al. |
| 2004/0002484 | A1 | 1/2004 | Hanson et al. |
| 2004/0142973 | A1 | 7/2004 | Castle |

FOREIGN PATENT DOCUMENTS

EP 0652004 10/1994
WO WO-01/27129 A1 4/2001

OTHER PUBLICATIONS

Raghow et al, Cancer Res 62, 1370-1376, Mar. 1, 2002.*
Clinical Trials, www.clinicaltrials.gov/clinicaltrials/PCI-00-105, 1-3, Jul. 1, 2001.*
Neubauer et al. Raloxifene (LY156758) Produces Antimetastatic Responses and Extends Survival in the PAIII Rat Prostatic Adenocarcinoma Model. The Prostate, 27:220-229 (1995).*

Lau et al. Expression of Estrogen Recpetor (ER)-a and ER-b in Normal and Malignant Prostatic Epithelial Cells: Regulation by Methylation and Involvement in Growth Regulation. Cancer Research, 60:3175-3182 (2000).*
Neubauer, B., et al., "Comparative Antitumor Effects of Hormonal Ablation, Estrogen Agonist, Estrogen Cytotoxic Derivative, and Antiestrogen in the PAIII Rat Prostatic Adenocarcinoma", Cancer Research 52, 4663-4671, 1992.
Neubauer, B. et al., "Raloxifene (LY156758) Produces Antimetastatic Responses and Extends Survival in the PAIII Rat Prostatic Adenocarcinoma Model", The Prostate 27:220-229 (1995).
Diaz, Michael, et al., "Management of Androgen-Independent Prostate Cancer", *Cancer Control*, vol. 11, No. 6 (2004) pp. 364-373.
Kim, Isaac Y., et al., "Raloxifene, a Mixed Estrogen Agonist/Antagonist, Induces Apoptosis in Androgen-independent Human Prostate Cancer Cell Lines", *Cancer Research* 62(18) (Sep. 15, 2002) pp. 5365-5369.

(Continued)

*Primary Examiner*—Ardin Marschel
*Assistant Examiner*—James D Anderson
(74) *Attorney, Agent, or Firm*—Seth D. Levy; Davis Wright Tremaine LLP (57) ABSTRACT

Disclosed herein is a method for treating and preventing prostate cancer, and particularly androgen-independent prostate cancer, the method including administering to a mammal a benzothiopene having the formula

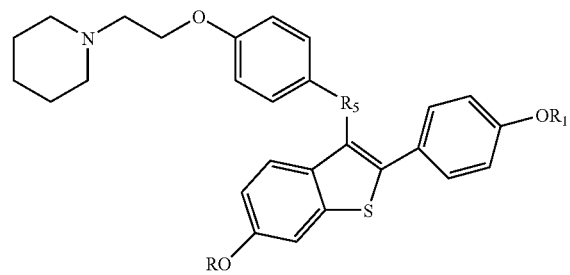

or pharmaceutically acceptable salts or prodrugs thereof, wherein R and $R_1$ are each independently selected from the group consisting of hydrogen, $-COR_2$, $-COR_3$, and $R_4$; $R_2$ is selected from the group consisting of hydrogen, C1-C14 alkyl, C1-C3 chloroalkyl, C1-C3 fluoroalkyl, C5-C7 cycloalkyl, C1-C4 alkoxy, and phenyl; $R_3$ is phenyl with at least one substitution selected from the group consisting of C1-C4 alkyl, C1-C4 alkoxy, hydroxy, nitro, chloro, fluoro, trichloromethyl, and trifluoromethyl; $R_4$ is selected from the group consisting of C1-C4 alkyl, C5-C7 cycloalkyl, and benzyl; and $R_5$ is selected from the group consisting of oxygen and $-C=O$. The method may further include the administration of an estrogen lowering drug to enhance efficacy of the compound of the present invention.

6 Claims, 6 Drawing Sheets
(4 of 6 Drawing Sheet(s) Filed in Color)

OTHER PUBLICATIONS

Database HCAPLUS on STN (Columbus, OH, USA) DN 137:363046, Agus, D., "Use of benzothiphenes to treat and prevent prostate cancer", WO 2002089801 A1, 20021114, abstract.
Database HCAPLUS on STN (Columbus, OH, USA) DN 138:66287, Kim, I. et al, Cancer Research, 2002, (62(13) 3649-3653, abstract.
Database HCAPLUS on STN (Columbus, OH, USA) DN 138:255252, Guzi, T. et al, "Preparation of substituted 1-benzhydryl-4-[2-(4-17-.beta.-hydroxysteroid dehydrogenase type 3 inhibitors for the treatment of androgen dependent diseases," WO 2003022835 A1, 20030320, abstract.

* cited by examiner

Raloxifene    Control    MCF-7 LNCaP

USE OF BENZOTHIOPENES TO TREAT AND PREVENT PROSTATE CANCER

This application is a continuation-in-part of U.S. patent application Ser. No. 10/142,087 filed May 9, 2002 now abandoned, the contents of which are hereby incorporated by reference.

FIELD OF THE INVENTION

Embodiments of the present invention are directed to methods for treating and preventing prostate cancer, in particular androgen-independent prostate cancer, by administering to a patient a benzothiopene, such as raloxifene or arzoxifene.

BACKGROUND OF THE INVENTION

Several types of cancer can affect the prostate gland, including adenocarcinoma, sarcoma, squamous cell carcinoma, and ductal transitional carcinoma. Adenocarcinoma is the most common of these and is one of the most common malignancies in men over 50 years old. In the United States, over 200,000 men become diagnosed with this type of cancer every year.

Most cancers of the prostate gland have androgen receptors. They depend on testosterone and other androgens for their growth. Hormone ablative therapy—therapy which chemically interferes with androgens or the organs that produce it—is therefore standard in the treatment of prostate cancer. Such therapy can prolong survival of men with prostate cancer from 3 to 5 years or more.

Chemical hormone ablative therapy includes the administration of drugs that block the hormonal pathways that lead to androgen synthesis. In the male, the hypothalamus secretes gonadotropin releasing hormone ("GnRH"), which stimulates the pituitary gland to secrete luteinizing hormone ("LH"); LH, in turn, stimulates the testes to produce testosterone. Synthetic analogs of GnRH and LH are therefore administered to reduce levels of androgens circulating within the body. These analogs compete with their natural counterparts for binding to GnrH receptors, thereby down-regulating the receptors and interrupting the testosterone production cycle. Estrogen also blocks androgen production, but can compromise cardiovascular health and so is rarely used. Antiandrogen drugs, such as flutamide, bicalutamide, or nilutamide, are also available. These bind to androgen receptors on prostate cancer cells, preventing their activation, and thereby limiting the action of natural androgens.

Surgical hormonal ablative therapy comprises surgical removal of one or both testes (orchiectomy), the testosterone-producing organ in the male. One may increase the effectiveness of this treatment still further by combining it with anti-androgens.

Androgen-independent prostate cancer (also called hormone refractory prostate cancer) does not depend on androgens for its growth; as a result, hormone ablative therapy has little effect on it. Even therapies that are highly effective at treating androgen-dependent cancers have been shown to be ineffective when applied to patients with androgen-independent cancer.

Androgen-independent cancer is difficult to treat. One can decrease the size of prostate inflammation associated with the cancer, such as with corticosteroids and other anti-inflammatory agents, but such treatment has no effect on the cancer itself. For this reason, a basic medical text still teaches that "There is no standard therapy for hormone refractory prostate cancer." M. H. Beers and R. Berkow, eds., Merck Manual of Diagnosis and Therapy, 1658 (1999). According to this text, cytotoxic and biologic agents "are being investigated," but "their superiority to corticosteroids alone has not been proved."

There is therefore a significant need in the art for a satisfactory treatment of androgen-independent prostate cancer. Such a treatment could have a dramatic impact on the health of older men, among whom prostate cancer is common.

SUMMARY OF THE INVENTION

It is an object of the present invention to provide a therapy for the treatment of prostate cancer, and in particular for the treatment of prostate cancer that responds poorly to hormone ablative therapy or does not respond to such therapy at all. In other words, it is an object of the present invention to provide a last hope, a therapy for the treatment of prostate cancer in those cases where patients have had—until now—little hope for long-term survival.

Disclosed herein is a method of treating prostate cancer that is surprisingly effective at treating androgen-independent prostate cancer, dramatically reversing the progression of the disease in patients previously diagnosed as having only months to live. The method comprises administering to patients an effective amount of a compound having the formula Formula I or pharmaceutically acceptable salts or prodrugs thereof. In a preferred embodiment, the compound is raloxifene; the compound of Formula I wherein R and $R_1$ are both hydrogen and $R_5$ is —C=O. In another preferred embodiment, the compound is arzoxifene; the compound of Formula I wherein R and $R_1$ are both hydrogen and $R_5$ is oxygen. An estrogen lowering drug (or drugs) may be administered in addition to a compound of the present invention; particularly in instances where a patient exhibits a serum estradiol level of greater than about 30 pg/ml.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1 depicts the inhibition of growth of androgen independent MSKPC9 tumor xenografts by raloxifene in accordance with an embodiment of the present invention.

FIG. 4 is executed in color and depicts a staining of a representative patient with disease that progressed during the course of a clinical study of raloxifene, described in greater detail in the ensuing Examples discussed herein, in accordance with an embodiment of the present invention. The representative patient exhibited moderate to strong expression of ER-β (FIG. 4A; 90% (1+) and 10% (2+)) and AR (FIG. 4C; 80% (1+), 12% (2+), 8% (0)), but an almost complete absence of nuclear staining for ER-α (FIG. 4B; 99% (0)).

FIG. 5 is executed in color and depicts a staining of a representative patient with disease that was stable during the course of a clinical study of raloxifene, described in greater detail in the ensuing Examples discussed herein, in accordance with an embodiment of the present invention.

FIG. 6 is executed in color and depicts an immunohistochemistry for positive controls in accordance with an embodiment of the present invention.

FIG. 7 is executed in color and depicts an immunohistochemistry for MSKPC9 xenograft tumors in accordance with an embodiment of the present invention.

DETAILED DESCRIPTION OF THE INVENTION

The method of the invention comprises administering to a patient an effective amount of a compound having the formula

Formula I or pharmaceutically acceptable salts thereof, wherein R and $R_1$ are each independently selected from the group consisting of hydrogen, —$COR_2$, —$COR_3$, and $R_4$; $R_2$ is selected from the group consisting of hydrogen, C1-C14 alkyl, C1-C3 chloroalkyl, C1-C3 fluoroalkyl, C5-C7 cycloalkyl, C1-C4 alkoxy, and phenyl; $R_3$ is phenyl with at least one substitution selected from the group consisting of C1-C4 alkyl, C1-C4 alkoxy, hydroxy, nitro, chloro, fluoro, trichloromethyl, and trifluoromethyl; $R_4$ is selected from the group consisting of C1-C4 alkyl, C5-C7 cycloalkyl, and benzyl; and $R_5$ is selected from the group consisting of oxygen and —C═O. Such compounds, as well as methods of preparing them, are described in detail in U.S. Pat. No. 4,418,068 ("the '068 patent"), the disclosure of which is hereby incorporated by reference. The '068 patent states that such compounds are useful for their antiestrogen and antiandrogen properties.

The inventor has made the surprising discovery that compounds of Formula I—known principally for their antiestrogen properties—may be used to treat androgen-independent prostate cancer; that is, that such compounds may be used to treat cancers that lack androgen receptors or otherwise do not depend on androgens for their growth. This discovery is particularly surprising in light of evidence that similar antiestrogens, most notably tamoxifen (tamoxifen citrate is available under the tradename NOLVADEX from AstraZenica Pharmaceuticals LP; Wilmington, Del.), have exhibited no effect on androgen-independent prostate cancer in several previous clinical trials. However, the methods of the present invention may be used in the treatment of androgen-dependent prostate cancer, as well.

The inventor has demonstrated that prostate cancer cells express the beta isoform of estrogen receptors, and hypothesizes that the mechanism of action of the compounds of Formula I is signaling through the beta isoform of the estrogen receptor. Preferred compounds of the invention are therefore those compounds of Formula I that are effective in blocking the beta isoform of the estrogen receptor. Tamoxifen is known to preferentially interact with the alpha isoform of the estrogen receptor.

An especially preferred compound for use with the method of the invention is raloxifene (available under the tradename EVISTA from Eli Lilly & Co.; Indianapolis, Ind.), a benzothiopene having the formula Formula II and pharmaceutically acceptable salts thereof. Raloxifene hydrochloride (raloxifene HCl) is the preferred salt of the compound of Formula II.

Another especially preferred compound for use with the method of the invention is arzoxifene, a benzothiopene having the formula Formula III In another embodiment of the invention, one administers to a mammal a prodrug of the compound of Formula I, or, preferably, a prodrug of the compound of Formula II or Formula III.

As used herein, the term "prodrug" refers to any compound that is converted into an active benziothiopene by metabolic processes within the body. There are various reasons why one might wish to administer a prodrug of the compounds of Formula I, II, or III rather than the compound itself. Depending on the particular compound (or its salt) that one uses, a prodrug might have superior characteristics as far as solubility, absorption, stability, release, toxicity, and patient acceptability are concerned. It should be readily apparent to one of ordinary skill in the art how one can make a prodrug of any compound of the invention. There are many strategies for doing so.

Prodrugs of the present invention include compounds having the formula

Formula IV or pharmaceutically acceptable salts thereof. $R_6$ and $R_7$ may be independently selected from the group consisting of hydrogen (such prodrugs are converted in vivo by enzymatic hydroxylation to active benzothiopenes), hydroxy and —$OR_8$, wherein $R_8$ is any suitable hydroxy protecting group that is metabolically cleaved in the body to yield a corresponding compound of the present invention, as described above with respect to Formulas I, II or III. Hydroxy protecting groups are described in Chapter 2 of T. W. Greene et al., *Protective Groups in Organic Synthesis*, $2^{nd}$ Ed., 1991. By way of example, simple ether and ester groups may be used as suitable hydroxy protecting groups in accordance with an embodiment of the present invention. Although an array of suitable protecting groups will be readily apparent to those of ordinary skill in the art, $R_8$ may additionally be selected from representative protecting groups including, but in no way limited to, C1-C4 alkyl, substituted or unsubstituted C1-C4 alkoxy, substituted or unsubstituted C1-C6 alkyl, $SO_2$—(C4-C6 alkyl) and —(CO)Ar in which Ar is benzyl or substituted phenyl (i.e., a phenyl group having one or more substituents selected from the group consisting of C1-C4 alkyl, C1-C4 alkoxy, hydroxy, nitro, bromo, chloro, fluoro, iodo, trichloromethyl and trifluoromethyl). The preparation of compounds illustrative of those used in connection with the methods of the present invention is described in PCT international patent publication No. WO 98/45288, the disclosure of which is hereby incorporated by reference. This publication describes the use of compounds related to those of the present invention in the treatment of androgen-dependent prostate cancer.

The administration of compounds of Formula I, II, III or IV (including their salts and prodrugs of these formulas) may be used as single agent therapy or as an adjuvant to established therapy, such as chemotherapy, surgery, or any other therapy known in the art to treat androgen-independent prostate cancer.

The appropriate dosage of the compounds of the invention depends on the age and weight of the individual to be treated, whether the compound is being used as single agent or adjuvant therapy, the type of androgen-independent cancer (e.g., whether it is an adenocarcinoma, sarcoma, squamous cell carcinoma, ductal transitional carcinoma, or other prostatic cancer), the progression of the cancer (e.g., whether it has metastasized or is localized), its size, location, and other factors well known to those skilled in the art of oncology. In general, doses of between 10 mg and 300 mg per day may be used. Although a dosage of 60 mg per day is sufficient to generate a clinically significant outcome in some patients (i.e., to treat the underlying disease condition or to merely prevent it from worsening), higher dosages may be desirable in cases where a patient does not respond to a dosage of 60 mg per day. The patient may be resistant or otherwise unresponsive to this level of treatment. A higher dosage of approximately 180 mg per day may be preferable in such cases, although a patient need not first exhibit resistance or unresponsiveness to a low dosage in order for an increased dosage to be efficacious or advisable. The administration of either raloxifene HCl, arzoxifene HCl or a prodrug thereof at a single dose of 60 mg per day or 180 mg per day is especially preferred in various embodiments of the present invention.

While not wishing to be bound by any particular theory, it is believed that the compounds of the present invention compete with endogenous estrogen for binding with the beta isoform of the estrogen receptor (ER-β). As such, in a further embodiment of the present invention, an estrogen lowering drug (or drugs) may be administered in addition to a compound of the present invention in either a treatment regimen or combination pharmaceutical product. Suitable estrogen lowering drugs will be readily recognized by those of skill in the art. They may include, by way of example, the class of compounds known as aromatase inhibitors. The additional administration of an estrogen lowering drug may be particularly desirable in cases where a patient exhibits a serum estradiol level of greater than about 30 pg/ml (normal males have a serum level of estradiol of between about 50 pg/ml and 70 pg/ml). Preclinical studies described in greater detail in the ensuing Examples demonstrated efficacy of ER-β targeting therapy only in the absence of estradiol or the presence of low levels of estradiol (e.g., less than about 30 pg/ml). While a complete absence of estradiol is not necessary to effect the methods of the present invention with the benzothiopene compounds described herein, it is believed that a reduced serum estradiol level (i.e., at or below about 30 pg/ml) enables significantly superior performance of the benzothiopene compounds in effecting their anti-tumor properties.

One preferably administers compounds of the invention orally, though one can also administer them by intravenous and intramuscular injection. In an especially preferred embodiment, one administers raloxifene HCl as a solid tablet containing 60 mg raloxifene HCl and excipients or 180 mg raloxifene HCl and excipients. In another especially preferred embodiment, one administers arzoxifene HCl as a solid tablet containing 60 mg arzoxifene HCl and excipients or 180 mg arzoxifene HCl and excipients.

Compounds of the invention are generally prepared by uniformly combining a compound of Formula I, II, III or IV with a pharmaceutically acceptable liquid carrier, a finely divided solid carrier, or both, and then shaping the product, if necessary. As used herein, "pharmaceutically acceptable carrier" refers to a carrier that is compatible with the other ingredients of the formulation and does not harm the subjects to which it is administered. Suitable such carriers include, for example, water, alcohols, natural or hardened oils and waxes, calcium and sodium carbonates, calcium phosphate, kaolin, talc, and lactose.

Formulations according to the invention are preferably combined with one or more excipients such as the following: preservatives, such as ethyl-p-hydroxybenzoate; suspending agents such as methyl cellulose, tragacanth, and sodium alginate; wetting agents such as lecithin, polyoxyethylene stearate, and polyoxyethylene sorbitan mono-oleate; granulating and disintegrating agents such as starch and alginic acid; binding agents such as starch, gelatin, and acacia; lubricating agents such as magnesium stearate, stearic acid, and talc; flavoring and coloring agents, and any other excipient conventionally added to pharmaceutical formulations.

Formulations of the present invention suitable for oral administration may be presented in any of the following forms: discrete units such as capsules, cachets, or tablets each containing a predetermined amount of the active ingredient; powder or granules; solutions or suspensions in an aqueous liquid or a non-aqueous liquid; or, as oil-in-water liquid emulsions or water-in-oil emulsions, and any other form suitable for oral administration.

EXAMPLES

The following examples are typical of the procedures that may be used to treat, in accordance with the methods of the invention, patients suffering from androgen-independent prostate cancer, or to evaluate the efficacy of compounds of the invention which may be used to treat such patients. Modifications of these examples will be readily apparent to those skilled in the art who seek to treat patients whose condition differs from those described herein.

Example 1

Treatment of Male Patients with
Androgen-Independent Prostate Cancer

Three male patients were selected for treatment on the basis of established diagnosis with prostate cancer. All three patients had failed standard androgen withdrawal therapy. Average prostate-specific antigen ("PSA") levels for each patient at the beginning of treatment was about 20-30 ng/ml. Hormone ablative therapy, in some cases aggressively administered as long as 36 months, had failed, manifested by a continued rise in PSA levels in each patient. The lack of response to such therapy indicated that the prostate cancer in each patient was (or had become) androgen-independent. Each patient continued to receive luteinizing hormone-releasing hormone ("LHRH")-agonist therapy, despite tumor growth in its presence. This is considered standard therapy, as tumor growth is likely to be more aggressive if testosterone levels were allowed to return to normal in these patients.

Each patient received orally 60 mg of raloxifene HCl once a day for a minimum of 30 days. PSA levels in each patient declined >50% in each patient after this period, demonstrating that raloxifene HCl can produce dramatically beneficial results in patients suffering from androgen-independent prostate cancer. The longest treated patient, as of the filing of the parent patent application, was 17 months since beginning therapy with a continued PSA <0.4 ng/ml and improvement in his bone scan. In the majority of patients treated with raloxifene, tumor stabilization occurred (non-progression), manifested by a leveling off of the previously rising serum PSA.

Example 2

Inhibition of Tumor Growth in
Androgen-Independent Xenograft Model

The inventor used an androgen-independent xenograft model of human prostate tumor cells (CWR22R) to raise tumors in male and female nude mice. Tumors developed over a period of 2-3 weeks into palpable masses. 10 mice were randomly assigned to a treatment group and 10 mice were assigned to a control group. 0.85 mg/kg of raloxifene HCl was administered daily by subcutaneous injection to each mouse in the treatment group. Mice in the control group received an injection of saline solution. After 30 days, tumors from surviving mice were surgically removed and visibly examined. Tumor size was reduced by 60% in mice from the treated group as compared to mice from the control group and female hosts.

Example 3

Preparation of Animal Subjects for Clinical Study

Xenograft studies were performed as described in D. B. Agus et al., "Response of prostate cancer to anti-Her-2/neu antibody in androgen-dependent and -independent human xenograft models," *Cancer Res.* 59(19):4761-4764 (1999). Orchiectomized seven- to eight-week-old nude athymic BALB/c male mice were obtained from the National Cancer Institute and maintained in pathogen-free conditions. Mice were inoculated subcutaneously ("s.c.") with minced tumor tissue together with MATRIGEL reconstituted basement membrane (available from BD Biosciences Discovery Labware; Bedford, Mass.) from the established androgen independent ("AI") MSKPC9 xenograft cell lines; cell lines are described in M. Nagabhushan et al., "CWR22: the first human prostate cancer xenograft with strongly androgen-dependent and relapsed strains both in vivo and in soft agar," *Cancer Res.* 56(13):3042-3046 (1996), and D. B. Agus et al., "Prostate cancer cell cycle regulators: response to androgen withdrawal and development of androgen independence," *J. Natl. Cancer Inst.* 91(21):1869-76 (1999).

Figure 1A:
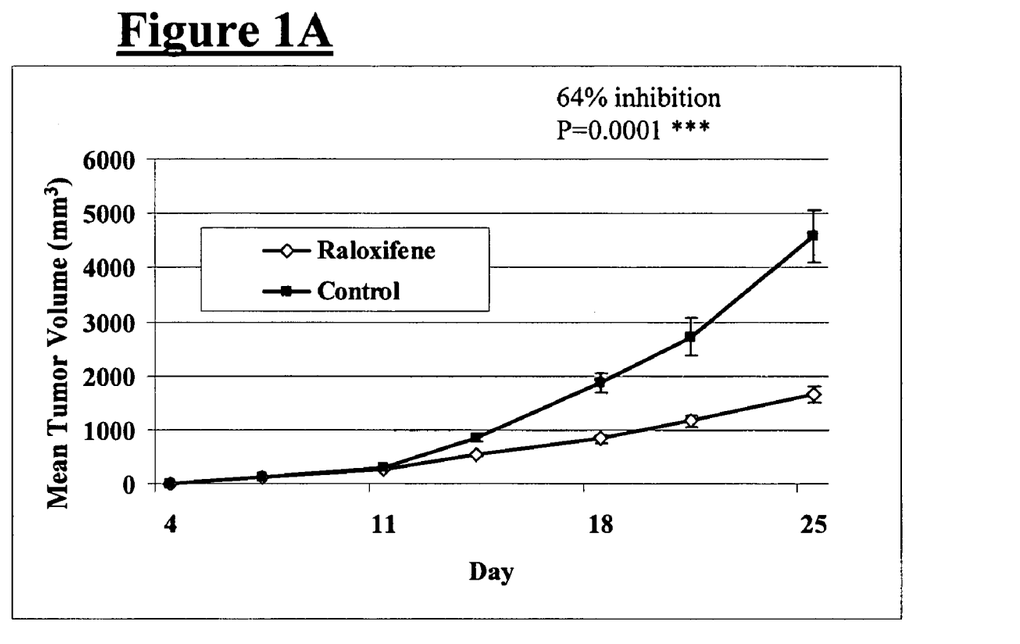
FIG. 1A illustrates a reduction in mean tumor volume for tumors treated with raloxifene as compared with those in the control group.
Figure 1B:
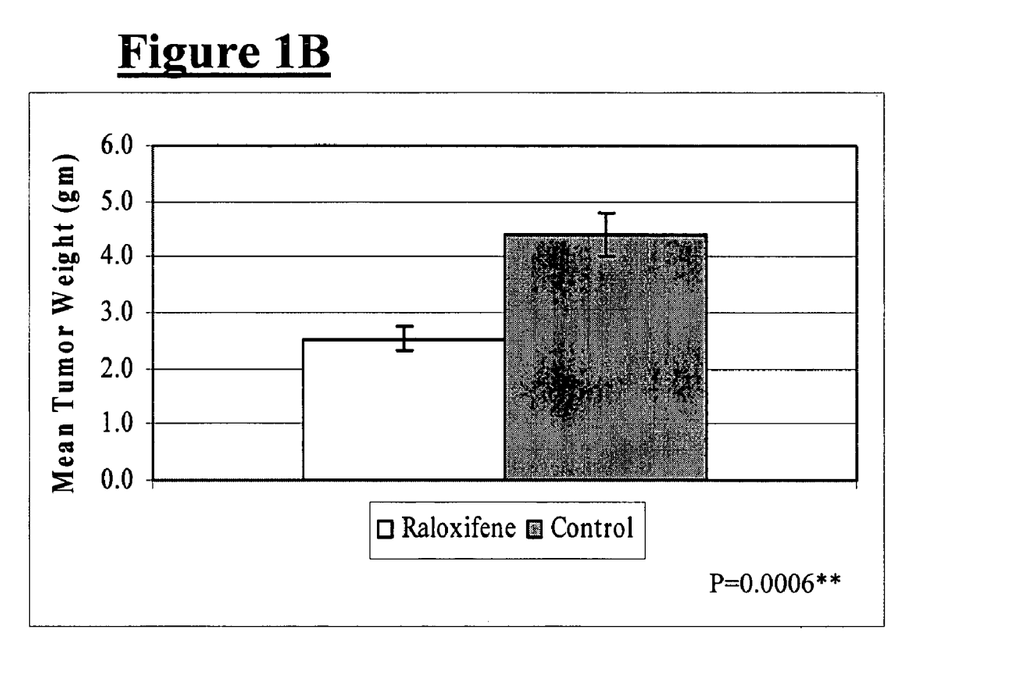
FIG. 1B similarly illustrates a reduction in mean tumor weight for tumors treated with raloxifene as compared with those in the control group.
Figure 2:
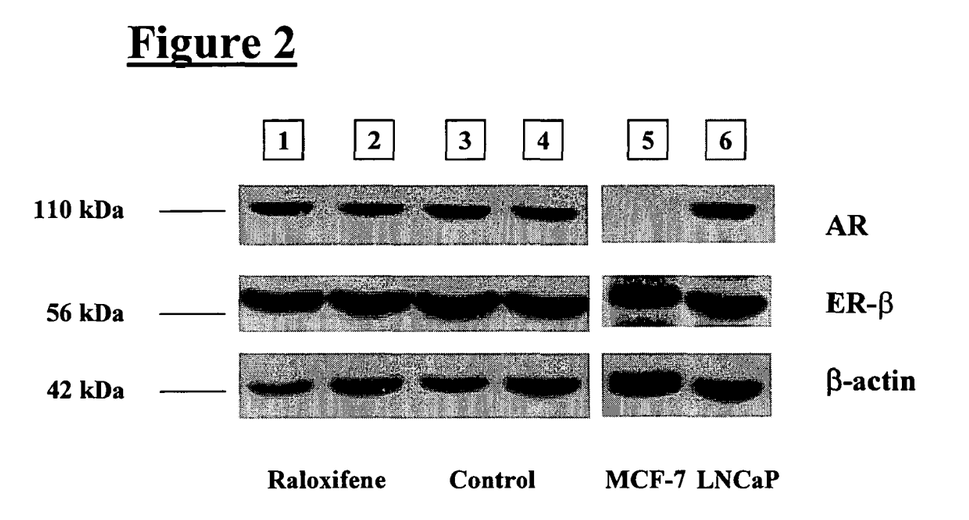
FIG. 2 depicts protein expression in MSKPC9 tumor xenografts in tumors treated with raloxifene as well as control tumors in accordance with an embodiment of the present invention. No ER-α protein expression was observed in the treatment groups, and no difference in androgen receptor ("AR") or ER-β mRNA was observed between treatment groups.

Animals with established tumors of at least 100 mm$^3$ in volume were designated to treatment groups that consisted of either raloxifene (40 mg/kg 5×/wk by oral gavage ("p.o.")) in 1.5% carboxymethylcellulose with 0.2% TWEEN-20 (obtained from Sigma Chemical, Co.; St. Louis, Mo.) or the vehicle alone at the same dosing schedule. Tumors were measured twice weekly with vernier calipers, and tumor volumes were calculated by the formula $(\pi/6)\times$(larger diameter)$\times$(smaller diameter)$^2$, described in M. F. Press et al., "HER-2/neu gene amplification characterized by fluorescence in situ hybridization: poor prognosis in node-negative breast carcinomas," *J. Clin Oncol.* 15(8):2894-2904 (1997). Animals were sacrificed 25 days post tumor inoculation and tumor tissue was snap frozen or fixed in paraffin for analysis. Results are illustrated in FIG. 1, which shows that tumors were smaller in animals treated with raloxifene.

Example 4

Determination of Serum PSA Levels

Figure 3:
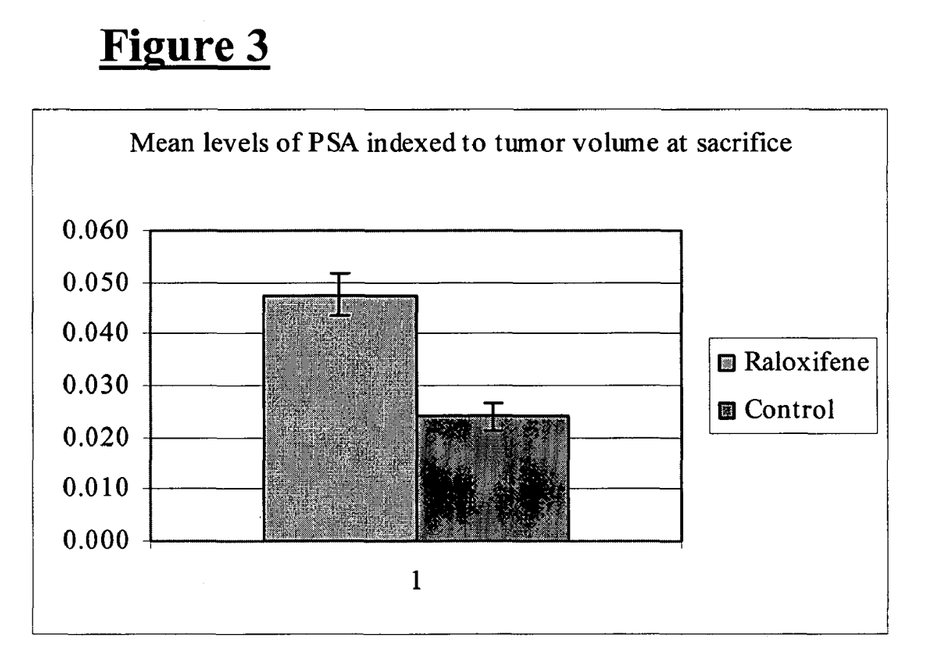
FIG. 3 depicts PSA (per tumor volume) increasing with raloxifene treatment in MSKPC9 tumor xenografts in accordance with an embodiment of the present invention.
Figure 4A:
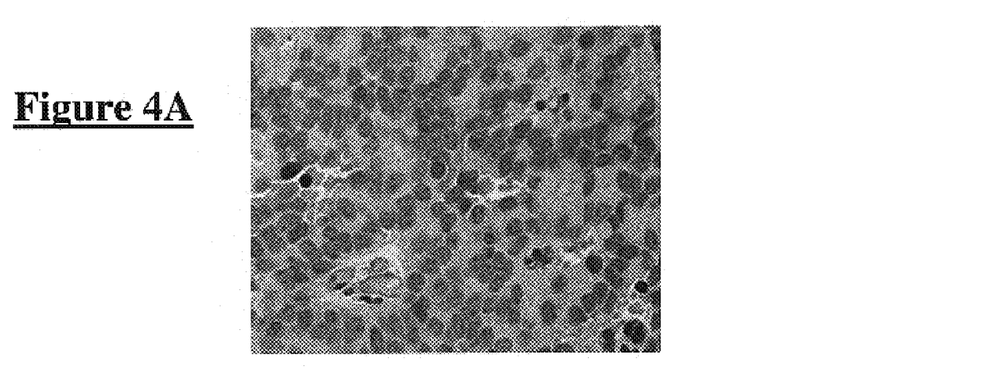
Figure 4B:
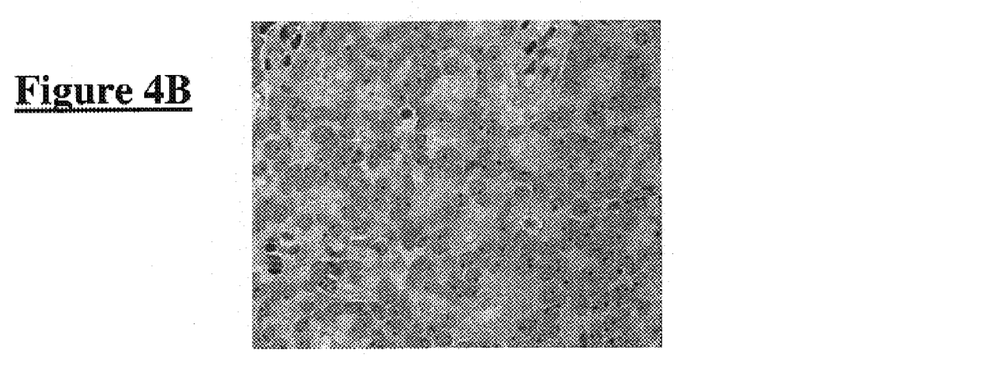
Figure 4C:
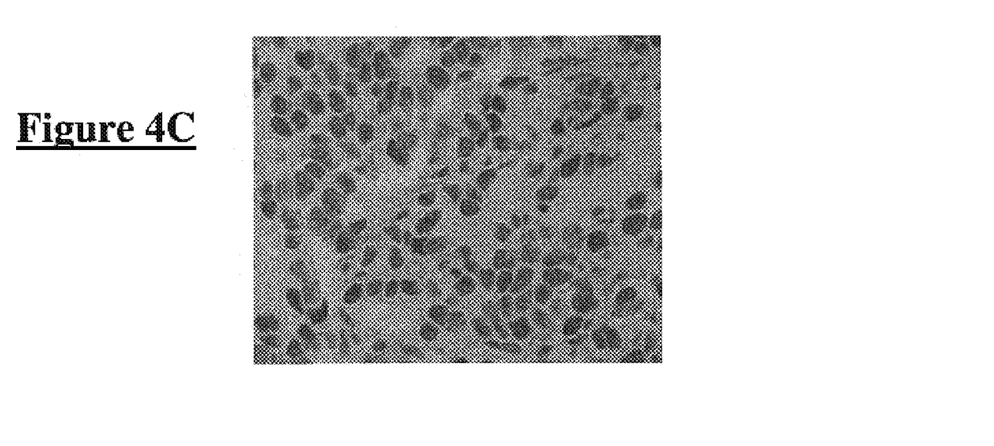
Figure 5A:
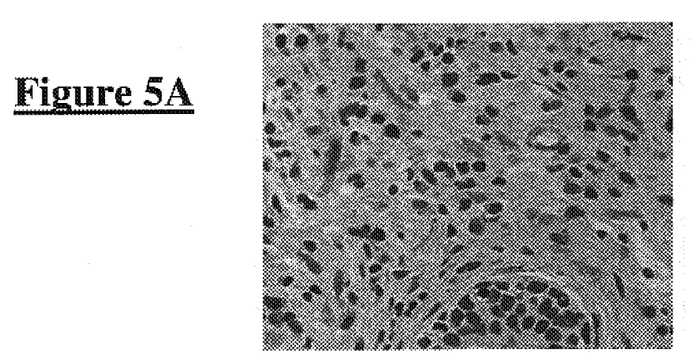
FIG. 5A illustrates the patient's expression of ER-β (50% (1+) and 50% (2+))
Figure 5B:
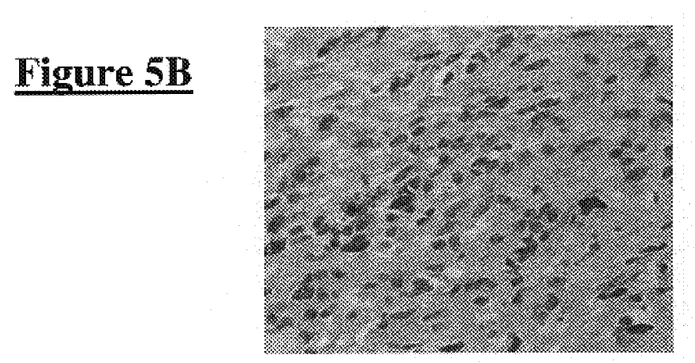
FIG. 5B illustrates the patient's expression of ER-α (26% (1+), 15% (2+), 59% (0))
Figure 5C:
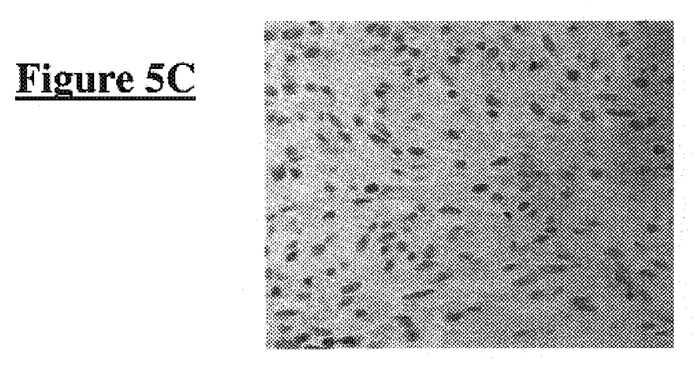
FIG. 5C illustrates the patient's expression of AR (42% (1+), 16% (2+), 43% (0)).
Figure 6A:
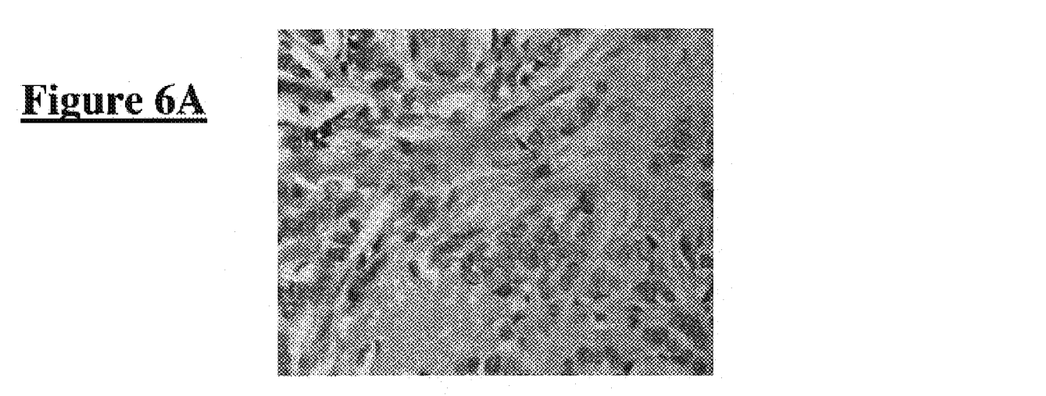
FIG. 6A illustrates tumor tissue without staining.
Figure 6B:
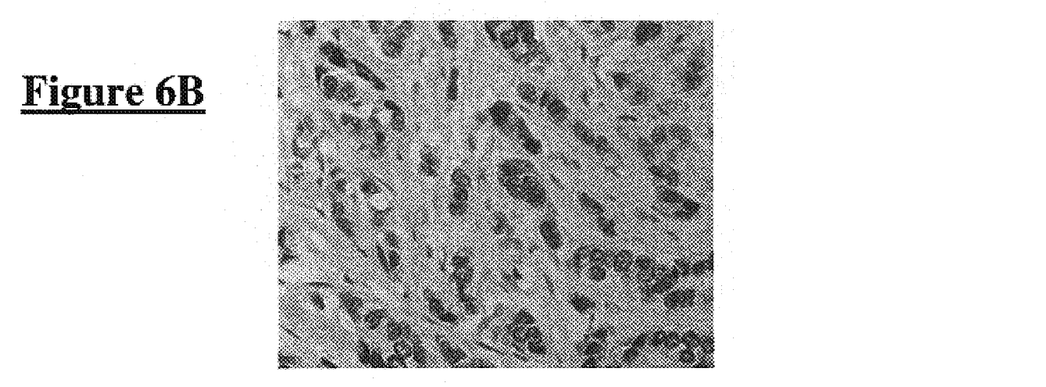
FIG. 6B illustrates tumor tissue expressing ER-α.
Figure 6C:
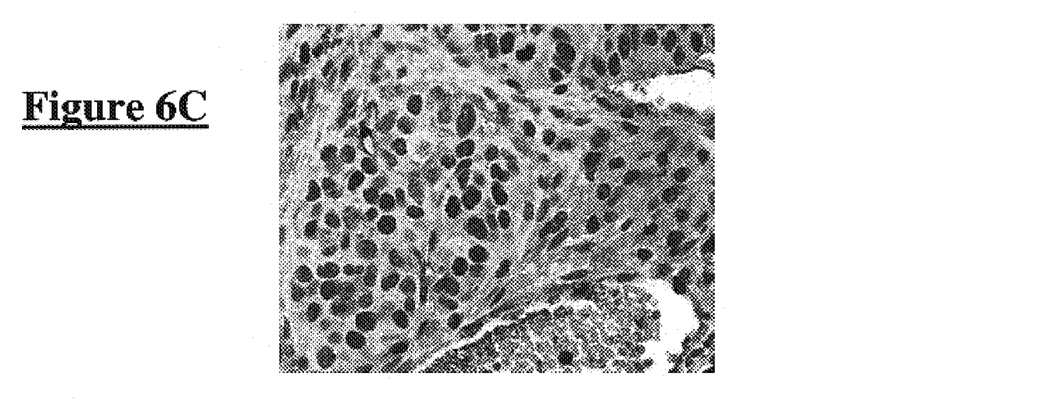
FIG. 6C illustrates tumor tissue expressing ER-β.
Figure 7A:
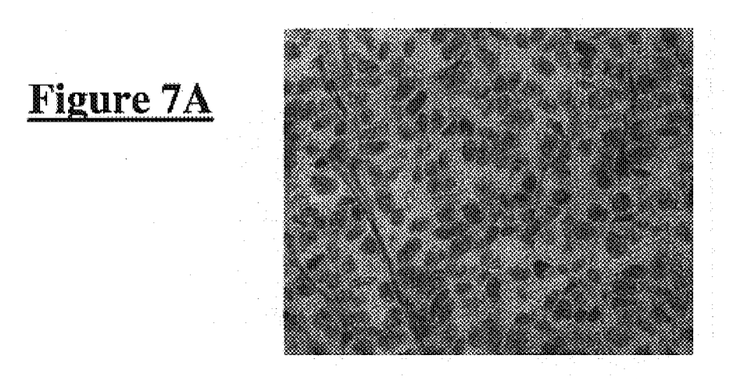
FIG. 7A illustrates staining for ER-β.
Figure 7B:
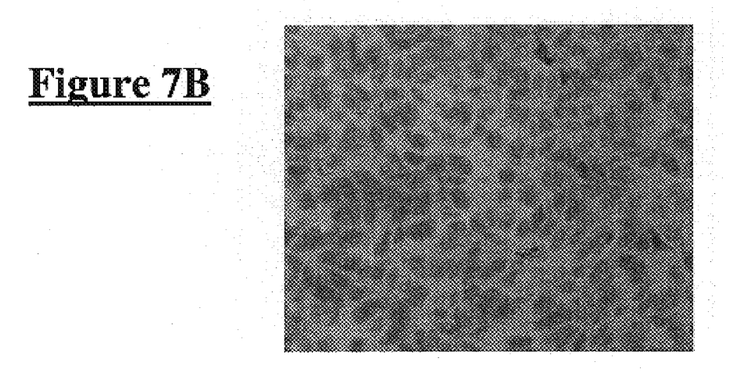
FIG. 7B illustrates staining for ER-α.
Figure 7C:
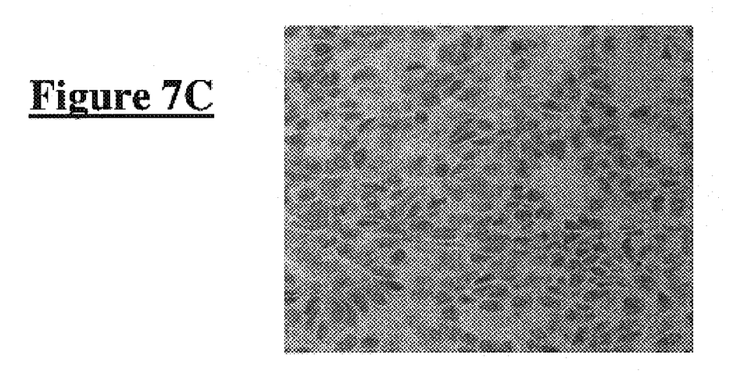
FIG. 7C illustrates staining for AR.

Levels of PSA in the blood of implanted animals were determined using an enzymatic immunoassay kit (obtained from American Qualex; San Clemente, Calif.). Blood samples were obtained prior to treatment by a small incision in the dorsal tail vein to collect 50 µl of blood using a serum-separator tube, or via a cardiac draw at sacrifice. Results of these assays are depicted in FIG. 3, which illustrates the rising PSA levels in animals treated with raloxifene.

Example 5

Immunoblot Analysis

Protein was extracted from the frozen tumor tissue by homogenizing and briefly sonicating the tissue in the protein extraction buffer (radioimmunoprecipitation ("RIPA") buffer, 5 µl/ml NaF, 5 µl/ml $Na_3VO_4$, 1 µl/ml protease inhibitor cocktail and 5 µl/ml phenylmethylsulfonyl fluoride ("PMSF")). LNCaP and MCF-7 cells were harvested and lysed with the same protein extraction buffer. Protein concentration was determined using the Bradford assay. The samples were boiled for five minutes and gel electrophoresis was carried out using 50 µg of total protein in each lane. After electrophoresis, protein was transferred to a 0.45-µm PVDF membrane (obtained from Pall Corp.; Ann Arbor, Mich.).

After the transfer, nonspecific binding sites were blocked by incubation in 5% milk in 1×TBST (i.e., Tris Buffered Saline with TWEEN) for one hour. Subsequently, membranes were incubated with 5% bovine serum albumin ("BSA") in 1×TBST containing the appropriate antibody (androgen receptor ("AR") 1:1000, ER-α 1:250, ER-β 1:250, β-actin 1:10,000; all antibodies obtained from Santa Cruz Biotechnology, Inc.; Santa Cruz, Calif.; hereinafter "Santa Cruz Biotechnology") overnight at 4° C. After washing with 1×TBST, membranes were incubated in the presence of rabbit (ER-α or ER-β) or mouse secondary antibody (AR, β-actin) at a dilution of 1:10,000 for one hour, and then developed using the ECL Western Blotting Analysis System (obtained from Amersham Biosciences, UK).

Example 6

RNA Extraction and Real-Time RT-PCR

Total RNA was extracted from prostate tumors using TRIZOL reagent (available from Invitrogen Corporation; Carlsbad, Calif.). DNase I (obtained from Ambion, Inc.; Austin, Tex.) was used to rid the samples of any extraneous DNA that might interfere with the reaction. The yield was quantified spectrophotometrically. Total RNA was reverse-transcribed into cDNA and PCR was performed in the same reaction by using TAQMAN One-Step RT-PCR Master Mix Reagents Kit (obtained from Applied Biosystems; Foster City, Calif.; hereinafter "Applied Biosystems"). Probes were labeled with 6-FAM on the 5' end and TAMRA on the 3' end. β-actin was used as the endogenous control and normalizer. The primer pairs used are depicted in Table 1, as follows:

TABLE 1

| | PCR Primer Pairs | | |
|---|---|---|---|
| | Forward | Reverse | Fluorescent Labeled Probe |
| AR | SEQ ID NO: 1 | SEQ ID NO: 2 | SEQ ID NO: 3 |
| ER-α | SEQ ID NO: 4 | SEQ ID NO: 5 | SEQ ID NO: 6 |
| ER-β | SEQ ID NO: 7 | SEQ ID NO: 8 | SEQ ID NO: 9 |
| β-actin | SEQ ID NO: 10 | SEQ ID NO: 11 | SEQ ID NO: 12 |

The PCR cycling conditions were performed for all of the samples as follows: 30 minutes at 48° C. for RT step; 10 minutes at 95° C. for AMPLITAQ GOLD Activation (available from Applied Biosystems); and 40 cycles for the melting (95° C., 15 seconds), and annealing/elongation (60° C. for one minute) steps. PCR reactions for each template were done in triplicate using 1 µg of total mRNA per sample. Each gene-specific primer pair was tested on standard 384-well plates. Standard curves were constructed using 10-1000 ng of total mRNA prepared from baseline CWR22R tumor lines. All of the experiments were optimized such that the threshold cycle ("$C_t$") from triplicate reactions did not span more than one cycle number.

The comparative $C_t$ method (PE Applied Biosystems) was used to determine relative quantification of gene expression for each gene compared with the β-actin control. This method is described in *PCR Applications: Protocols for Functional Genomics*, ed. M. Innis et al., Acad. Press. (1999). First, the $C_t$ values from the β-actin reactions were averaged for each triplicate. Next, the $C_t$ values from the gene-of-interest reactions were averaged. The gene-of-interest average was divided by the β-actin average to take into account the variability of total RNA. Finally, values of gene expression for raloxifene-treated tumors were compared to values from tumors from animals that were not administered any compound Example 7

Histopathology

Human and xenograft tissues were fixed in 10% buffered formalin and embedded in paraffin, and 5-µm sections were incubated for 20 minutes in DAKO Target Retrieval Solution, High pH (obtained from Dako Corp.; Carpinteria, Calif.; hereinafter "Dako") and stained with 1:100 mouse anti-human AR (obtained from Dako), rabbit anti-ER-α (obtained from BioGenex Laboratories, Inc.; San Ramon, Calif.) or rabbit anti-ER-β antibody (obtained from Santa Cruz Biotechnology). Slides were then incubated for 30 minutes with DAKO EnVision System HRP Mouse or Rabbit (obtained from Dako) and exposed with DAB Peroxidase Substrate Kit (obtained from Vector Laboratories, Inc.; Burlingame, Calif.). Positive fields were scored by counting different fields and more than 500 cells. Data were recorded in a continuum as the percentage of cells stained and the intensity of staining was graded as follows: 0, undetectable; 1+, moderate staining; 2+ strong staining. A specimen was considered as a "positive" result if at least 10% or more of the cells had nuclear staining. Data generated in accordance with this and the aforementioned Examples are presented in FIGS. 4-7.

Example 8

Selection of Patients for Clinical Study

The protocol implemented in the ensuing Example was approved by the Cedars-Sinai Institutional Review Board. All the patients enrolled in the study gave written informed consent prior to any study procedures being performed.

Between August 2001 and July 2002, twenty-one patients were enrolled into the study at the Prostate Cancer Center of Cedars-Sinai Medical Center in Los Angeles, Calif. Patients who were eligible for the study were men who had histologically confirmed adenocarcinoma of the prostate and confirmed disease progression after hormonal therapy. Patients were required to have progression of disease as evidenced by CT scan or rising PSA on two successive measurements after discontinuation of anti-androgen therapy. In addition, patients receiving androgen receptor-blocking agents as their last form of therapy had to have confirmed disease progression after drug withdrawal. Nonsurgically castrated patients continued to receive LHRH agonist while on study to maintain castrate levels of serum testosterone.

Both patients with measurable disease by either bone scan or CT scan, and evaluable disease evidenced by rising PSA were included in the study. Patients whose only evidence of disease progression was rising PSA had to have an increasing PSA on any two determinations drawn at two least weeks apart, with a greater than 20% increase from the baseline value. Other eligibility criteria included: Karnofsky performance status >70%, life expectancy >12 weeks (with at least four weeks since major surgery or radiation therapy), and at least 12 weeks for treatment with strontium-89, rhenium, or samarium-153. Required laboratory values included white blood cell ("WBC") count greater than 3000 µL, granulocytes greater that 1,500 µL, platelets greater than 100,000/µL, hemoglobin greater than 9.0 g/dL, creatinine less than 1.5 times the upper limit of normal ("ULN"), aspartate transaminase ("AST") and alanine transaminase ("ALT") less than two times the UNL, sodium between 130 and 148 mmol/L, potassium between 3.3 and 5.2 mmol/L, chloride between 90 and 110 mmol/L, and calcium between 8.0 and 10.5 mg/dL. Patients with a history of uncontrolled or severe cardiovascular disease (e.g., inadequately uncontrolled hypertension, congestive heart failure, angina, or myocardial infarction within the previous year), a history of thromboembolism, a history of biliary colic or untreated cholethiasis were excluded. Patients with brain metastasis, clinical signs of brain involvement or leptomeningeal disease, dementia, psychoses, or other significant impairment of mental status were excluded. Patients with a history of another malignancy during the past five years (other than non-melanomatous skin cancer or in situ stage T1a bladder cancer), patients with active infections requiring antibiotics, or patients on concurrent commercial or investigational antineoplastic therapies were excluded. No concomitant use of prostata or saw palmetto was permitted.

Example 9

Response Criteria

Response to therapy was assessed after the first two months of therapy and then monthly thereafter. Toxicity was assessed monthly at each study visit. A complete response ("CR") required resolution of all signs of disease for a duration of at least one month (i.e., normalization of PSA; resolution of all indicator lesions by physical examination or radiographic studies with no appearance of new lesions; decline of serum PSA to <0.1 ng/ml in patients who had had a prostatectomy and <0.5 mg/ml in patients who had had prostatic radiotherapy; all abnormal biochemical parameters must have returned to normal, and during this time there should have been no cancer-associated deterioration in weight, performance status, or symptoms). A partial response ("PR") required a decrease by >50% of the sum of the products of the perpendicular diameters for all measurable lesions lasting at least one month, no appearance of new lesions, and a reduction in serum PSA by >50% on two consecutive occasions at least one month apart. For patients being evaluated by bone metastases, a PR required a reduction in serum PSA by >50% on two consecutive occasions at least one month apart an improvement in bone scan (reduction in intensity or size of one or more metastatic foci and no new foci of radionuclide uptake unless due to osteoclastic healing documented on plain radiograph, CT scan, or MRI scan). During this time there should have been no cancer-associated deterioration in weight, performance status, or symptoms. Progressive disease ("PD") was defined by any of the following: (1) increase >25% in the sum of the products of the perpendicular diameters of bidimensionally measurable lesions in the sum of the transverse diameters of unidimensionally measurable lesions, (2) the appearance of new lesions, and (3) by the increase in serum PSA >50% over baseline as documented on two successive measurements >28 days apart. For patients with bone metastases, a PR could also be defined by an increase in size and intensity of radionuclide uptake of lesions previously seen on baseline bone scan or the appearance of two or more new foci of abnormal uptake (unless due to osteoclastic healing as described above) or any indication for radiotherapy to bone areas after the patient has begun treatment with raloxifene. For PD to be scored by PSA criteria alone, a confirmatory PSA determination was required and obtained two weeks after the value representing a >50% increase. Patients who had improvement in one objective parameter while meeting the criteria for PD by another parameter were scored as having PD. Patients who did not experience a response or exhibit PD were scored as having stable disease ("SD"), if they remained clinically stable for a period of at least three months.

Example 10

Wisconsin Brief Pain Inventory

At baseline, each patient was asked if he had bone pain related to the prostate cancer. Patients who answered affirmatively were asked to complete the Wisconsin Brief Pain Inventory at baseline and at each monthly follow-up visit thereafter.

Example 11

Treatment

Treatment consisted of 60 mg oral raloxifene daily (obtained from Eli Lilly & Company; Indianapolis, Ind.). Treatment was administered with monthly lab draws and follow-up visits with the physician. To counteract the increase risk of deep vein thrombosis that the estrogenic properties of raloxifene poses, patients were administered a regimen of low dose COUMADIN (warfarin sodium; available from DuPont Pharma; Wilmington, Del.). Patients received 1 mg oral COUMADIN daily (or 0.5 mg oral COUMADIN daily if patients were already taking aspirin).

Example 12

Characteristics of Patients in Clinical Study

Patient characteristics are listed in Table 2. A total of twenty-one patients with prostate cancer were enrolled into the study with a median age of 73 years. Patients had a median Karnofsky performance status of 90% (range, 70-100%). 15/21 (71%) patients had evidence of bone disease. Six patients (28.6%) had evidence of measurable disease, nine patients (42.8%) had evaluable/non-measurable disease with bone metastases, and six patients (28.6%) had rising PSA levels only. A majority (67%) of patients had Gleason scores 8-10 at the time of biopsy. Prostate specimens were from either biopsies (14, 67%) or prostatectomy's (7, 33%). The median time from diagnosis of prostate cancer to study entry was 83.3 months (range, 16.6-209.5 months).

TABLE 2

Patient Baseline Characteristics

| Characteristics | Number | Percentage (%) |
|---|---|---|
| Number in Study | 21 | N/A |
| Age (yr) | | |
| Median | 72.7 | N/A |
| Range | 62-92 | N/A |
| Karnofsky Performance Status | | |
| Median | 90 | N/A |
| 100 | 5 | 24 |
| 90 | 8 | 38 |
| 80 | 7 | 33 |
| 70 | 1 | 5 |
| Weight at Entry (kg) | | |
| Median | 81.8 | |
| Range | 63-132 | |
| Site of Disease | | |
| Osseous | 15 | 71.4 |
| Lymph Nodes | 5 | 23.8 |
| Rectum/Bladder | 1 | 4.8 |
| PSA | | |
| Median | 48.9 | N/A |
| Range | 1-886.0 | N/A |
| Hemoglobin (mg/dl) | | |
| Median | 12.7 | N/A |
| Range | 9.9-14.5 | N/A |
| Alkaline Phosphatase (u/l) | | |
| Median | 91 | N/A |
| Range | 55-239 | N/A |
| Gleason Score | | |
| 2 + 2 | 1 | 5.3 |
| 2 + 3 | 2 | 10.5 |
| 3 + 4 | 2 | 10.5 |
| 3 + 5 | 3 | 15.8 |
| 4 + 3 | 4 | 21.1 |
| 4 + 5 | 4 | 21.1 |
| 5 + 3 | 1 | 5.3 |
| 5 + 4 | 2 | 10.5 |
| Time from diagnosis of prostate cancer to study entry (months) | | |
| Median | 83.3 | N/A |
| Range | 16.6-209.5 | N/A |

N/A = not applicable

Prior treatment is listed in Table 3. All patients received prior treatment with combined androgen blockade. 19 (95%) received secondary hormone therapy with thirteen (62%) patients receiving more than two hormonal therapies prior to the study. Previous non-hormonal treatments included local surgery (57%), local radiation (38%), and chemotherapy (33%). Patients received a median of 4.0 (range, 1-9) prior systemic treatments. All patients enrolled in the study failed their prior treatments and were determined to have AIPC.

TABLE 3

Prior Treatments

| Treatment | Number | Percentage (%) |
|---|---|---|
| Local Therapy | | |
| Surgical | 12 | 57 |
| Radiation | 8 | 38 |
| Systemic Therapy | | |
| Hormone Therapy | | |
| Total | 21 | 100 |
| Secondary | 20 | 95 |
| >2 Regimens | 13 | 62 |
| Mode of Castration | | |
| Surgical | 3 | 14.3 |
| Medical | 18 | 85.7 |
| Chemotherapy | | |
| Total | 6 | 28.5 |
| 1 Regimen | 2 | 9.5 |
| >1 Regimen | 4 | 19 |
| Prior Systemic Treatments | | |
| Median | 4.0 | N/A |
| Range | 1-9 | N/A |

N/A = not applicable

Example 13

Toxicity

Previous clinical studies indicate that raloxifene is well tolerated and the most common adverse events reported were hot flashes and leg cramps (EVISTA package insert; Eli Lilly & Co.). Similarly, we observed that raloxifene was well tolerated with most drug related toxicities reported being mild (grade 1-2). Toxicities are listed in Table 4. The reported urinary tract infection ("UTI") (1) and hematuria (1) were thought to be related to the patient's underlying disease. Two grade 3 events were reported: a grade 3 arthralgia/myalgia thought to be related to the patient's recent injury, and a grade 3 elevated creatinine that was attributed to the patient's disease progression. A grade 4 hyperglycemia was reported, however, that patient had a documented grade 3 hyperglycemia prior to beginning treatment; the hyperglycemia was therefore not attributed to the study drug.

TABLE 4

Patients Experiencing Drug-Related Toxicity*

| | Grade | | | |
|---|---|---|---|---|
| Toxicity | 1 | 2 | 3 | 4 |
| Blood/Bone Marrow | | | | |
| Anemia | 2 | 1 | | |
| Cardiovascular | | | | |
| Hypotension | | 1 | | |
| Edema | 1 | | | |

TABLE 4-continued

Patients Experiencing Drug-Related Toxicity*

| Toxicity | Grade | | | |
|---|---|---|---|---|
| | 1 | 2 | 3 | 4 |
| Constitutional Symptoms | | | | |
| Fatigue/Malaise | 1 | 1 | | |
| Dermatology/Skin | | | | |
| Rash | 1 | | | |
| Endocrine | | | | |
| Hot flashes | 2 | | | |
| Hyperglycemia | 1 | | 1 | |
| Hypoglycemia | 1 | | | |
| Gastrointestinal | | | | |
| Nausea/Vomiting | 1 | 1 | | |
| Diarrhea | 1 | | | |
| Constipation | | 2 | | |
| Hemorrhage | | | | |
| Hematuria | 1 | | | |
| Hepatic | | | | |
| Increased Alkaline Phosphatase | 3 | | | |
| Increased SGOT (AST) | 1 | | | |
| Hypoalbuminemia | 2 | | | |
| Infection | | | | |
| UTI | 1 | | | |
| Metabolic/Laboratory | | | | |
| Bicarbonate | 1 | | | |
| Hypercholesterolemia | 2 | | | |
| Hypertriglyceridemia | | 1 | | |
| Pain | | | | |
| Arthralgia/Myalgia | 2 | | 1 | |
| Bone Pain | 1 | 1 | | |
| Renal | | | | |
| Increased Creatinine | 1 | | 1 | |

*divided by NCI's Common Toxicity Criteria, v2.0

Example 14

Patient Response and Survival

Of the twenty-one patients enrolled, seventeen patients (81%) patients reached the first evaluation time point and were included in the efficacy analysis. Four patients did not reach evaluation time point; two withdrew from the study at their own request due to (1) emotional side effects, and (1) change in medical care. The third patient was withdrawn from the study due to non-compliance (1), and the fourth patient was withdrawn because he required radiation to bony areas for pain relief (although this fourth patient was included in the efficacy analysis and was considered as disease progression).

At the first evaluation time point, thirteen of the eighteen patients had progressive disease and were discontinued from the study, while five of eighteen patients had stable disease and were continued on raloxifene. Disease progression was defined as rising PSA (12) and required radiation to bony area (1). No progression of soft tissue or osseous disease was observed. Of the five patients with stable disease, four patients were discontinued due to progressive disease (i.e., rising PSA) at the second evaluation point. The other patient remained on study with stable disease. No improvement in soft tissue or bone disease was observed.

Median time to disease progression on raloxifene was 8.3 weeks (range, 2.9-24.71). At the time of analysis (November, 2002), the median potential off study follow-up time was 9.0 months. Median survival was 10.5 months. As of July, 2003, 19 of 21 (90%) patients are alive.

Example 15

Histopathology

Of the twenty-one patients enrolled in the study, thirteen patients had existing prostate tissue available for analysis of ER-α, ER-β and AR expression. Moderate to strong expression of ER-β and AR was detected in all of the cases (100%, 13/13). Almost complete absence of ER-α nuclear staining was seen in all except for two out of thirteen (15%) patients. Fifty percent of the surrounding stromal tissue stained positive for both estrogen receptors in all of the patients. Due to the small number of available specimens no significant differences were detected between groups of patients that progressed during the first round of treatment and those that exhibited stable disease.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A method of inhibiting the rate of growth of an androgen-independent prostate cancer tumor in a mammal in need thereof, the method comprising administering to the mammal an effective amount of a compound having the formula or pharmaceutically acceptable salts thereof, wherein the compound is administered in an effective amount of about 180 mg to about 300 mg per day.

2. The method of claim 1, further comprising administering to the mammal an estrogen lowering drug in an amount effective to lower the serum level of estradiol in the mammal.

3. The method of claim 1, wherein the compound is administered in an effective amount of about 180 mg per day.

4. The method of claim 2, wherein the estrogen lowering drug is administered in an amount effective to lower the serum level of estradiol in the mammal to an amount no greater than 30 pg/ml.

5. A method of inhibiting the rate of growth of an androgen-independent prostate cancer tumor in a mammal in need thereof, the method comprising administering to the mammal an effective amount of a compound having the formula or pharmaceutically acceptable salts thereof; and administering to the mammal an estrogen lowering drug in an amount effective to lower the serum level of estradiol in the mammal.

6. The method of claim 5, wherein the estrogen lowering drug is administered in an amount effective to lower the serum level of estradiol in the mammal to an amount no greater than 30 pg/ml.

* * * * *

SEQUENCE LISTING

```
<160> NUMBER OF SEQ ID NOS: 12

<210> SEQ ID NO 1
<211> LENGTH: 19
<212> TYPE: DNA
<213> ORGANISM: Unknown
<220> FEATURE:
<223> OTHER INFORMATION: PCR Primer

<400> SEQUENCE: 1
```
cgacttcacc gcacctgat                                             19

<210> SEQ ID NO 2
<211> LENGTH: 20
<212> TYPE: DNA
<213> ORGANISM: Unknown
<220> FEATURE:
<223> OTHER INFORMATION: PCR Primer

<400> SEQUENCE: 2
tgggataggg cactctgctc                                            20

<210> SEQ ID NO 3
<211> LENGTH: 21
<212> TYPE: DNA
<213> ORGANISM: Unknown
<220> FEATURE:
<223> OTHER INFORMATION: PCR Primer

<400> SEQUENCE: 3
tgtggtaccc tggcggcatg g                                          21

<210> SEQ ID NO 4
<211> LENGTH: 21
<212> TYPE: DNA
<213> ORGANISM: Unknown
<220> FEATURE:
<223> OTHER INFORMATION: PCR Primer

<400> SEQUENCE: 4
tggtggagat cttcgacatg c                                          21

<210> SEQ ID NO 5
<211> LENGTH: 22
<212> TYPE: DNA
<213> ORGANISM: Unknown
<220> FEATURE:
<223> OTHER INFORMATION: PCR Primer

<400> SEQUENCE: 5
ctcctctccc tgcagattca tc                                         22

<210> SEQ ID NO 6
<211> LENGTH: 25
<212> TYPE: DNA
<213> ORGANISM: Unknown
<220> FEATURE:
<223> OTHER INFORMATION: PCR Primer

<400> SEQUENCE: 6
ctggctacat catctcggtt ccgca                                      25

<210> SEQ ID NO 7
<211> LENGTH: 18
<212> TYPE: DNA
<213> ORGANISM: Unknown
<220> FEATURE:
<223> OTHER INFORMATION: PCR Primer

<400> SEQUENCE: 7
cacttgctga acgccgtg                                              18

<210> SEQ ID NO 8
<211> LENGTH: 18
<212> TYPE: DNA
<213> ORGANISM: Unknown

```
<220> FEATURE:
<223> OTHER INFORMATION: PCR Primer

<400> SEQUENCE: 8
gggaggagat gccgctct                                                 18

<210> SEQ ID NO 9
<211> LENGTH: 25
<212> TYPE: DNA
<213> ORGANISM: Unknown
<220> FEATURE:
<223> OTHER INFORMATION: PCR Primer

<400> SEQUENCE: 9
ccgatgcttt ggtttgggtg attgc                                         25

<210> SEQ ID NO 10
<211> LENGTH: 17
<212> TYPE: DNA
<213> ORGANISM: Unknown
<220> FEATURE:
<223> OTHER INFORMATION: PCR Primer

<400> SEQUENCE: 10
gcgcggctac agcttca                                                  17

<210> SEQ ID NO 11
<211> LENGTH: 22
<212> TYPE: DNA
<213> ORGANISM: Unknown
<220> FEATURE:
<223> OTHER INFORMATION: PCR Primer

<400> SEQUENCE: 11
tctccttaat gtcacgcacg at                                            22

<210> SEQ ID NO 12
<211> LENGTH: 18
<212> TYPE: DNA
<213> ORGANISM: Unknown
<220> FEATURE:
<223> OTHER INFORMATION: PCR Primer

<400> SEQUENCE: 12
caccacggcc gagcggga                                                 18
```